US011741754B2

(12) United States Patent
Balaji et al.

(10) Patent No.: US 11,741,754 B2
(45) Date of Patent: Aug. 29, 2023

(54) DETECTING AND VALIDATING A USER ACTIVITY CAPTURED FROM MULTIPLE SENSORS (71) Applicant: Tata Consultancy Services Limited, Mumbai (IN)

(72) Inventors: Ramesh Balaji, Chennai (IN); Srinivasa Raghavan Venkatachari, Chennai (IN); Harish Kumar Dhanasekaran, Chennai (IN)

(73) Assignee: Tata Consultancy Services Limited, Mumbai (IN)

( * ) Notice: Subject to any disclaimer, the term of this patent is extended or adjusted under 35 U.S.C. 154(b) by 260 days.

(21) Appl. No.: 17/164,662

(22) Filed: Feb. 1, 2021

(65) Prior Publication Data
US 2021/0321894 A1 Oct. 21, 2021

(30) Foreign Application Priority Data

Apr. 20, 2020 (IN) .............................. 202021016926

(51) Int. Cl.
*G06V 40/00* (2022.01)
*G06V 40/20* (2022.01)
(Continued)

(52) U.S. Cl.
CPC .......... *G06V 40/25* (2022.01); *A61B 5/02438* (2013.01); *A61B 5/1118* (2013.01);
(Continued)

(58) Field of Classification Search
CPC ........ A61B 2562/0219; A61B 5/02438; A61B 5/1118; A61B 5/7267; G06V 10/811;
(Continued)

(56) References Cited

U.S. PATENT DOCUMENTS

2014/0307927 A1* 10/2014 Folmer ................ A61B 5/4866
382/107
2015/0092980 A1* 4/2015 Folmer ................ G06V 40/165
382/103
(Continued)

FOREIGN PATENT DOCUMENTS

EP 2391972 B1 5/2015
EP 3086320 A1 10/2016

OTHER PUBLICATIONS

A. K. Bourke, E. A. F. Ihlen, P. Van de Ven, J. Nelson and J. L. Helbostad, "Video analysis validation of a real-time physical activity detection algorithm based on a single waist mounted tri-axial accelerometer sensor," 2016 38th Annual International Conference of the IEEE Engineering in Medicine and (Year: 2016).*
(Continued)

*Primary Examiner* — Carl H Layno
*Assistant Examiner* — Michael J Lau
(74) *Attorney, Agent, or Firm* — Finnegan, Henderson, Farabow, Garrett & Dunner, LLP (57) ABSTRACT Conventionally, activity detection has been through one mode i.e., smart watch. Though it works in reasonable cases, there are chances of false positives considerably. Other approaches include surveillance which limits itself to object detection. Embodiments of present disclosure provide systems and methods for detecting activities performed by user from data captured from multiple sensors. A first input (FI) comprising accelerometer data, heart rate and gyroscope data and second input (SI) comprising video data are obtained. Features are extracted from FI and pre-processed for a first activity (FA) detection using activity prediction model. Frames from SI are processed for creating bounding box of user and resized thereof to extract pose coordinates vector. Distance between vector of pose coordinates and training vectors of pose coordinates stored in the system is
(Continued)

computed and a second activity (SA) is detected accordingly. Both the FA and SA are validated for determining true and/or false positive.

14 Claims, 4 Drawing Sheets (51) Int. Cl.
    *A61B 5/024*     (2006.01)
    *A61B 5/11*     (2006.01)
    *A61B 5/00*     (2006.01)
    *G06V 10/764*     (2022.01)
    *G06V 10/776*     (2022.01)
    *G06V 10/80*     (2022.01)
    *G06V 20/40*     (2022.01)
    *G06V 40/10*     (2022.01)

(52) U.S. Cl.
    CPC .......... *A61B 5/7267* (2013.01); *G06V 10/764* (2022.01); *G06V 10/776* (2022.01); *G06V 10/811* (2022.01); *G06V 20/41* (2022.01); *G06V 40/103* (2022.01); *A61B 2562/0219* (2013.01)

(58) Field of Classification Search
    CPC .... G06V 10/776; G06V 10/764; G06V 20/41; G06V 40/25; G06V 40/103
    USPC ....................................................... 600/508
    See application file for complete search history.

(56) References Cited

U.S. PATENT DOCUMENTS

| | | | |
|---|---|---|---|
| 2015/0313529 A1* | 11/2015 | Nevo ................... | A61B 5/4809 600/595 |
| 2016/0065984 A1 | 3/2016 | Nejat et al. | |
| 2016/0081607 A1* | 3/2016 | el Kaliouby ........... | G16H 40/67 434/236 |
| 2020/0074154 A1* | 3/2020 | el Kaliouby ......... | A61B 5/7267 |

OTHER PUBLICATIONS

Yan Wang, Shuang Gang, Hongnian Yu, A survey on wearable sensor modality centred human activity recognition in health care, Expert Systems with Applications, vol. 137, 2019, pp. 167-190, ISSN 0957-4174 (Year: 2019).*

Rahman, Shah Atiqur & Leung, Karhang & Cho, David. (2012). Recognising Human Actions by Analyzing Negative Spaces. IET Computer Vision. 6. 197-213. 10.1049/iet-cvi.2011.0185. (Year: 2012).*

Taffoni, Fabrizio et al.; "A Wearable System for Real-Time Continuous Monitoring of Physical Activity", Journal of Healthcare Engineering, 2018, Hindawi, https://downloads.hindawi.com/journals/jhe/2018/1878354.pdf.

* cited by examiner

DETECTING AND VALIDATING A USER ACTIVITY CAPTURED FROM MULTIPLE SENSORS

PRIORITY CLAIM

This U.S. patent application claims priority under 35 U.S.C. § 119 to: India Application No. 202021016926, filed on Apr. 20, 2020. The entire contents of the aforementioned application are incorporated herein by reference.

TECHNICAL FIELD

The disclosure herein generally relates to activity detection and validation techniques, and, more particularly, to detecting and validating a user activity captured from multiple sensors.

BACKGROUND

Elderly population is steadily increasing in most countries due to a decline in birth and mortality rates. The population of independently living senior citizens has also become significant. This has led to an active research focus in geriatric wellness. Apart from the usual physical and cognitive decline that proceeds with age, there are much softer aspects such as dignity and ability to live independently (age-in-place), If subjects are monitored all the time by instrumenting them heavily, technology can possibly predict and prevent many abnormal situations. In today's environment, most of the activity detection i.e., walking, eating, typing the keyboard etc. takes place through wearable device/smartwatches and the like. Performing the activity detection only through one mode i.e., smart watch, though it works in reasonable cases, however there are chances of false positives considerably.

SUMMARY

Embodiments of the present disclosure present technological improvements as solutions to one or more of the above-mentioned technical problems recognized by the inventors in conventional systems. For example, in one aspect, there is provided a processor implemented method for activities detection and validation thereof. The method comprises: obtaining, via one or more hardware processors, (i) accelerometer data, heart rate data and gyroscope data from a wearable device associated with a user, (ii) video data captured from an image capturing device, the video data comprising information associated with the user; detecting, via the one or more hardware processors, a first activity of the user from each of the accelerometer data, the heart rate data and the gyroscope data obtained from the wearable device associated with the user by: extracting a plurality of features from the accelerometer data, heart rate data and the gyroscope data and pre-processing thereof to obtain a set of pre-processed features; and detecting, via an activity detection model executed by the one or more hardware processors, the first activity being performed by the user, using the set of pre-processed features; detecting, via the one or more hardware processors, a second activity of the user from the video data captured from the image capturing device by: processing each frame from the video data to extract a bounding box of the user; resizing the bounding box of the user to obtain a resized bounding box; detecting and extracting a vector of pose coordinates from the resized bounding box; computing, via a Chebyshev Distance technique, a distance between (i) the vector of pose coordinates and (ii) one or more training vectors of pose coordinates stored in a database to obtain a plurality of distances; and detecting the second activity based on the plurality of computed distances; and validating, via the one or more hardware processors, the first activity and the second activity based on a comparison of (i) the first activity predicted based on the accelerometer data, the heart rate data and the gyroscope data from the wearable device associated with the user and an associated timestamp and (ii) the second activity predicted based on the video data captured from the image capturing device and an associated timestamp, to obtain a true positive or a false positive.

In an embodiment, the plurality of features are extracted from at least one of (i) a mean of the accelerometer data, the mean of the heart rate data and the mean of the gyroscope data, (iii) a standard deviation of the accelerometer data, the standard deviation of the heart rate data and the standard deviation of the gyroscope data.

In an embodiment, the activity detection model is generated by: obtaining accelerometer data, heart rate data and gyroscope data from the wearable device associated with the user; extracting a set of features from the obtained accelerometer data, the heart rate data and the gyroscope data; pre-processing the obtained set of features to obtain a pre-processed feature set; and generating, using a classifier, the activity detection model based on a set of training features obtained from the pre-processed feature set, wherein the activity detection model is applied on a remaining set of features serving as a set of test features obtained from the pre-processed features set to determine an accuracy of activity prediction.

In an embodiment, the step of resizing the bounding box of the user to obtain a resized bounding box is based on a specification of each frame comprised in the video data.

In an embodiment, the one or more training vectors of pose coordinates are obtained by: obtaining training video data that is captured from the image capturing device, wherein the training video data comprises information specific to one or more users; tagging an activity label for each activity identified in one or more frames comprised in the training video data; processing each of the one or more frames comprised in the training video data to extract a bounding box of the one or more users; and generating the one or more training vectors of pose coordinates using the bounding box of the one or more users.

In an embodiment, the step of detecting a second activity based on the plurality of computed distances comprises: performing a comparison of each computed distance across the plurality of computed distances; and detecting the second activity based on the comparison.

In an embodiment, the true positive indicates that the first activity and the second activity are identical.

In an embodiment, the false positive indicates that the first activity and the second activity are different from each other.

In another aspect, there is provided a system for activities detection and validation thereof. The system comprises: a memory storing instructions; one or more communication interfaces; and one or more hardware processors coupled to the memory via the one or more communication interfaces, wherein the one or more hardware processors are configured by the instructions to: obtain (i) accelerometer data, heart rate data and gyroscope data from a wearable device associated with a user, (ii) video data captured from an image capturing device, the video data comprising information associated with the user; detect a first activity of the user from each of the accelerometer data, the heart rate data and the gyroscope data obtained from the wearable device associated with the user by: extracting a plurality of features from the accelerometer data, the heart rate data and the gyroscope data and pre-processing thereof to obtain a set of pre-processed features; and detecting, via an activity detection model, the first activity being performed by the user, using the set of pre-processed features; detect a second activity of the user from the video data captured from the image capturing device by: processing each frame from the video data to extract a bounding box of the user; resizing the bounding box of the user to obtain a resized bounding box; detecting and extracting a vector of pose coordinates from the resized bounding box; computing, via a Chebyshev Distance technique, a distance between (i) the vector of pose coordinates and (ii) one or more training vectors of pose coordinates stored in a database to obtain a plurality of distances; and detecting the second activity based on the plurality of computed distances; and validate, the first activity and the second activity based on a comparison of (i) the first activity predicted based on the accelerometer data, the heart rate data and the gyroscope data from the wearable device associated with the user and an associated timestamp and (ii) the second activity predicted based on the video data captured from the image capturing device and an associated timestamp, to obtain a true positive or a false positive.

In an embodiment, the plurality of features are extracted from at least one of (i) a mean of the accelerometer data, the mean of heart rate data and the mean of the gyroscope data, (iii) a standard deviation of the accelerometer data, the standard deviation of the heart rate data and the standard deviation of the gyroscope data.

In an embodiment, the activity detection model is generated by: obtaining accelerometer data, heart rate data and gyroscope data from the wearable device associated with the user; extracting a set of features from the obtained accelerometer data, the heart rate data and the gyroscope data; pre-processing the obtained set of features to obtain a pre-processed feature set; and generating, using a classifier, the activity detection model based on a set of training features obtained from the pre-processed feature set, wherein the activity detection model is applied on a remaining set of features serving as a set of test features obtained from the pre-processed features set to determine an accuracy of activity prediction.

In an embodiment, the step of resizing the bounding box of the user to obtain a resized bounding box is based on a specification of each frame comprised in the video data.

In an embodiment, the one or more training vectors of pose coordinates are obtained by: obtaining training video data that is captured from the image capturing device, wherein the training video data comprises information specific to one or more users; tagging an activity label for each activity identified in one or more frames comprised in the training video data; processing each of the one or more frames comprised in the training video data to extract a bounding box of the one or more users; and generating the one or more training vectors of pose coordinates using the bounding box of the one or more users.

In an embodiment, the step of detecting a second activity based on the plurality of computed distances comprises: performing a comparison of each computed distance across the plurality of computed distances; and detecting the second activity based on the comparison.

In an embodiment, the true positive indicates that the first activity and the second activity are identical.

In an embodiment, the false positive indicates that the first activity and the second activity are different from each other.

In yet another embodiment, there is provided a computer program product comprising a non-transitory computer readable medium having a computer readable program embodied therein, wherein the computer readable program, when executed on a computing device, causes the computing device to detect activities and validate thereof by: obtaining, via one or more hardware processors of the computing device, (i) accelerometer data, heart rate data and gyroscope data from a wearable device associated with a user, (ii) video data captured from an image capturing device, the video data comprising information associated with the user; detecting, via the one or more hardware processors, a first activity of the user from each of the accelerometer data, the heart rate data and the gyroscope data obtained from the wearable device associated with the user by: extracting a plurality of features from the accelerometer data, heart rate data and the gyroscope data and pre-processing thereof to obtain a set of pre-processed features; and detecting, via an activity detection model executed by the one or more hardware processors, the first activity being performed by the user, using the set of pre-processed features; detecting, via the one or more hardware processors, a second activity of the user from the video data captured from the image capturing device by: processing each frame from the video data to extract a bounding box of the user; resizing the bounding box of the user to obtain a resized bounding box; detecting and extracting a vector of pose coordinates from the resized bounding box; computing, via a Chebyshev Distance technique, a distance between (i) the vector of pose coordinates and (ii) one or more training vectors of pose coordinates stored in a database to obtain a plurality of distances; and detecting the second activity based on the plurality of computed distances; and validating, via the one or more hardware processors, the first activity and the second activity based on a comparison of (i) the first activity predicted based on the accelerometer data, the heart rate data and the gyroscope data from the wearable device associated with the user and an associated timestamp and (ii) the second activity predicted based on the video data captured from the image capturing device and an associated timestamp, to obtain a true positive or a false positive.

In an embodiment, the plurality of features are extracted from at least one of (i) a mean of the accelerometer data, the mean of the heart rate data and the mean of the gyroscope data, (iii) a standard deviation of the accelerometer data, the standard deviation of the heart rate data and the standard deviation of the gyroscope data.

In an embodiment, the activity detection model is generated by: obtaining accelerometer data, heart rate data and gyroscope data from the wearable device associated with the user; extracting a set of features from the obtained accelerometer data, the heart rate data and the gyroscope data; pre-processing the obtained set of features to obtain a pre-processed feature set; and generating, using a classifier, the activity detection model based on a set of training features obtained from the pre-processed feature set, wherein the activity detection model is applied on a remaining set of features serving as a set of test features obtained from the pre-processed features set to determine an accuracy of activity prediction.

In an embodiment, the step of resizing the bounding box of the user to obtain a resized bounding box is based on a specification of each frame comprised in the video data.

In an embodiment, the one or more training vectors of pose coordinates are obtained by: obtaining training video data that is captured from the image capturing device, wherein the training video data comprises information specific to one or more users; tagging an activity label for each activity identified in one or more frames comprised in the training video data; processing each of the one or more frames comprised in the training video data to extract a bounding box of the one or more users; and generating the one or more training vectors of pose coordinates using the bounding box of the one or more users.

In an embodiment, the step of detecting a second activity based on the plurality of computed distances comprises: performing a comparison of each computed distance across the plurality of computed distances; and detecting the second activity based on the comparison.

In an embodiment, the true positive indicates that the first activity and the second activity are identical.

In an embodiment, the false positive indicates that the first activity and the second activity are different from each other.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIGS. 1 through 4C, where similar reference characters denote corresponding features consistently throughout the figures, there are shown preferred embodiments and these embodiments are described in the context of the following exemplary system and/or method.

Figure 1:
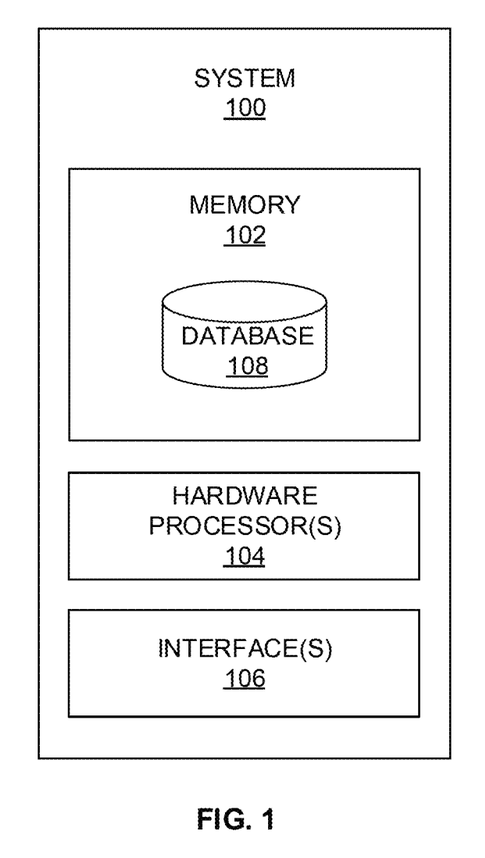
FIG. 1 depicts a system for detecting activity performed by a user and validating thereof using data captured from multiple sensors, in accordance with an embodiment of the present disclosure.

FIG. 1 depicts a system 100 for detecting activity performed by a user and validating thereof using data captured from multiple sensors, in accordance with an embodiment of the present disclosure. In an embodiment, the system 100 includes one or more hardware processors 104, communication interface device(s) or input/output (I/O) interface(s) 106 (also referred as interface(s)), and one or more data storage devices or memory 102 operatively coupled to the one or more hardware processors 104. The one or more processors 104 may be one or more software processing components and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is/are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, a database 108 is comprised in the memory 102, wherein the database 108 comprises information on human activities that are captured by multiple sensors (e.g., sensors can include wearable device(s), image capturing device(s) and the like). The sensory information captured by multiple sensors may include, for example, but not limited to, (i) accelerometer data, heart rate data and gyroscope data from the wearable device (e.g., smartwatch, or health monitoring devices connected to subjects/humans/users), and (ii) video data captured from image capturing device such as a camera and the like. In an embodiment, the sensory data/information can also be collected from a mobile communication device such as a smart phone wherein the accelerometer data, the heart rate data and the gyroscope data associated with user performing activities are captured and video is captured through an in-built camera of the smart phone. Such information may be periodically transmitted to a system (e.g., the system 100) for further processing and analysis.

The information stored in the database 108 may further comprise information on time-series data (or coordinates in x, y, and z-axes) obtained from (i) the accelerometer data, the heart rate data and the gyroscope data from the wearable device (e.g., smartwatch, or health monitoring devices connected to subjects/humans/users), and (ii) video data, and the like. The database 108 may further comprise (i) training data associated with detection of human activity using accelerometer data, heart rate data and gyroscope data, and (ii) training data associated with human activity captured using a camera. The memory 102 further stores pose coordinates (e.g., (i) vector of pose coordinates of an incoming video data, and (ii) training vector pose coordinates associated with training video data) and the like. Further, the memory 102 may store activity prediction model that is generated using the training data associated with accelerometer, heart rate and gyroscope data collected. In an embodiment, techniques and/or machine learning models such as classifiers as known in the art are comprised in the memory 102 and invoked as per the requirement to perform the methodologies described herein. More specifically, Chebyshev distance, support vector machine(s) classifier, random forest classifier and the like may be comprised in the memory 102 and are invoked as per the requirement to perform the methodologies described herein. The memory 102 further comprises (or may further comprise) information pertaining to input(s)/output(s) of each step performed by the systems and methods of the present disclosure. In other words, input(s) fed at each step and output(s) generated at each step are comprised in the memory 102 and can be utilized in further processing and analysis.

Figure 2:
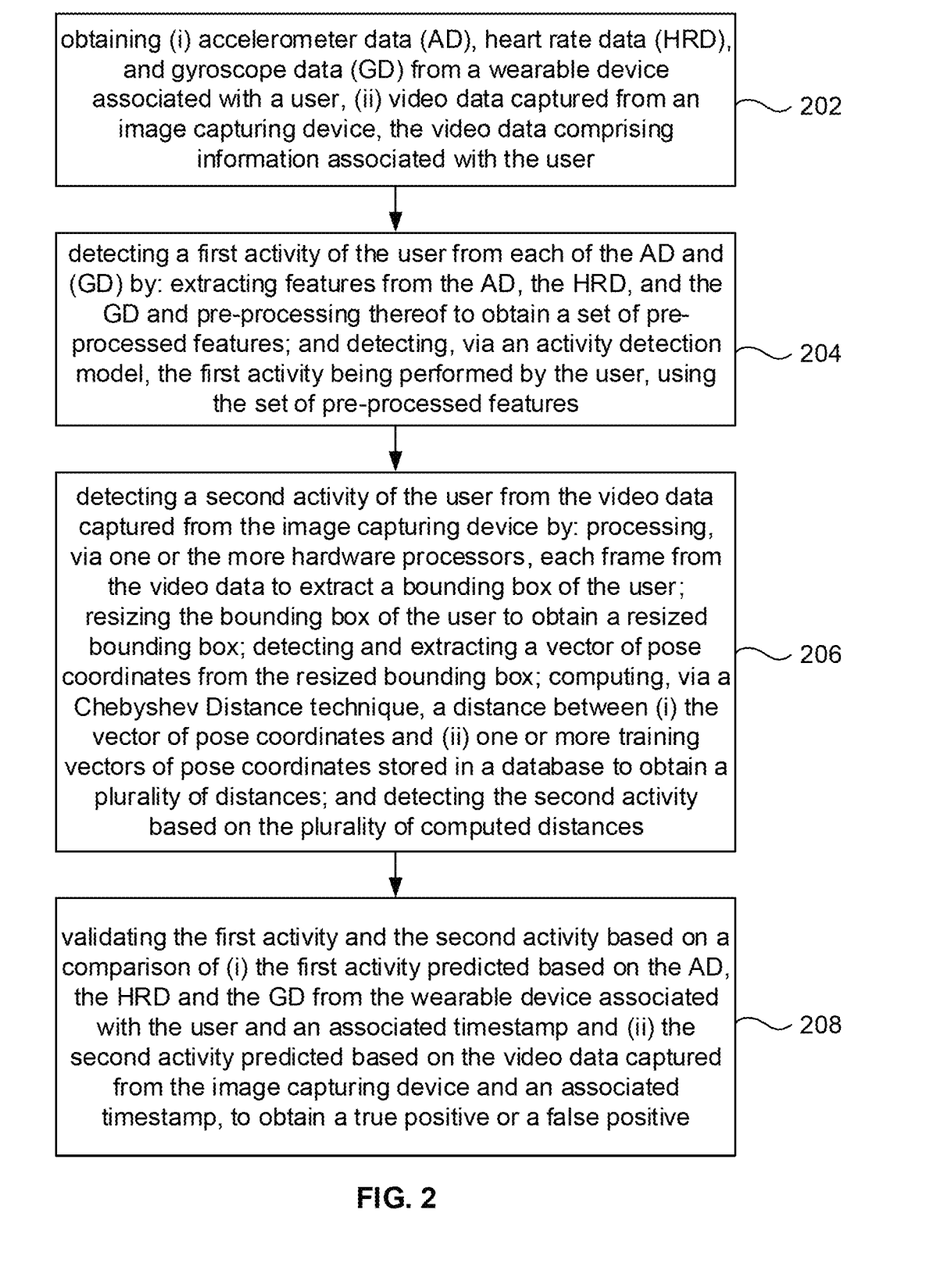
FIG. 2 depicts an exemplary flow chart illustrating a method for detecting activity performed by a user and validating thereof using data captured from multiple sensors, using the system of FIG. 1, in accordance with an embodiment of the present disclosure.

FIG. 2, with reference to FIG. 1, depicts an exemplary flow chart illustrating a method for detecting activity performed by a user and validating thereof using data captured from multiple sensors, using the system 100 of FIG. 1, in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to components of the system 100 of FIG. 1, the flow diagram as depicted in FIG. 2 and FIGS. 3A through 4C. In an embodiment, at step 202 of the present disclosure, the one or more hardware processors 104 obtain (i) accelerometer data, heart rate data and gyroscope data from a wearable device associated with a user, (ii) video data captured from an image capturing device, the video data comprising information associated with the user. Prior to obtaining the (i) accelerometer data, heart rate data and gyroscope data from a wearable device associated with a user, (ii) video data captured from an image capturing device, the system 100 is trained with training dataset and an activity prediction model is generated for activities detection and validation thereof. Below description is provided for better understanding of the embodiments of the present disclosure, the embodiments pertain to training methodology used herein for training the system 100.

Initially, for training, the system 100 obtains accelerometer data, heart rate data and gyroscope data from the wearable device associated with one or more users. Smartwatch is one of the most popular and most widely used wearable devices. Smartwatches are well suited for gathering data that can classify user activities in real-time, as it is used by many people and is constantly worn on the body. A wrist-worn smartwatch provides more valuable information on user behavior through sensing the movements of that hand. Accordingly, smartwatch worn by elderly person (or user whose activity is being detected and validated) transmits accelerometer, heart rate and gyroscope data every 'x' seconds (e.g., say 10 seconds) to the system 100 which is equipped with Machine learning techniques that detects specific activities for example, eating, sitting, walking, sleeping, and the like. In the present disclosure, values of the acceleration and gyroscope on the x, y, and z axes and heart rate values are collected as input by the system 100. Mean and standard deviation values of acceleration and gyroscope data on the x, y, and z axes are obtained as shown in Tables 1 and 2 respectively and mean and standard deviation of heart rate (or heart rate data) is shown in Table 3 respectively.

TABLE 1

| acc_meanx | acc_sdx | acc_meany | acc_sdy | acc_meanz | acc_sdz |
|---|---|---|---|---|---|
| −2.757885172 | 0.733945836 | −6.536901445 | 2.221579738 | 5.77999589 | 3.67387148 |
| −3.364356957 | 0.968903112 | −7.174649031 | 1.027233335 | 5.844892184 | 1.885662959 |
| −3.30651833 | 1.487663588 | −6.061478956 | 2.251668163 | 5.962309723 | 3.615430264 |
| −3.444166028 | 1.258369434 | −6.930097749 | 2.331023821 | 5.234384091 | 2.991029242 |
| ... | ... | ... | ... | ... | ... |
| −2.193710775 | 1.340403643 | −7.271763788 | 2.426678854 | 5.10142532 | 3.579929698 |
| −2.229332299 | 1.401865642 | −7.361850304 | 2.304509117 | 4.526816803 | 4.210521661 |

TABLE 2

| gy_meanx | gy_sdx | gy_meany | gy_sdy | gy_meanz | gy_sdz |
|---|---|---|---|---|---|
| 3.001600183 | 62.26205098 | 0.146299998 | 14.52389675 | 0.146299998 | 12.99672521 |
| 2.674699946 | 47.74314399 | 2.763600058 | 16.73000116 | 2.763600058 | 16.90300874 |
| 5.382300019 | 80.50873994 | 0.21069987 | 20.72447551 | 0.21069987 | 35.25913666 |
| −2.964499855 | 73.51082241 | 7.519399997 | 21.85662546 | 7.519399997 | 27.81334118 |
| ... | ... | ... | ... | ... | ... |
| 7.180600132 | 84.87770972 | 0.652400105 | 35.27231169 | 0.652400105 | 20.74550794 |
| 0.807500003 | 69.92786625 | 3.013333311 | 18.58950764 | 3.013333311 | 15.72474995 |

TABLE 3

| meanhr | sdhr |
|---|---|
| 77.98 | 30.28596375 |
| 95.34 | 0.764460594 |
| 96.79 | 1.177242541 |
| 93.58 | 0.695413546 |
| ... | ... |
| 111.57 | 0.636474666 |
| 109.3571429 | 12.03827513 |

In many of the scenarios, the accelerometer data, gyroscope data and the heart rate data arrive in the form of mean and standard deviation values. In some scenarios, the accelerometer data, gyroscope data and the heart rate data may arrive in raw data form, wherein the system 100 performs certain operations to obtain mean and standard deviations of these values. Features are extracted from the obtained values of acceleration and gyroscope on the x, y, and z axes along with heart rate values. Features are extracted from at least one of (i) a mean of the accelerometer data, (ii) the mean of the heart rate data (iii) the mean of the gyroscope data, (i) a standard deviation of the accelerometer data, (ii) the standard deviation of the heart rate data (iii) the standard deviation of the gyroscope data and are provided in below Table 4 (accelerometer values), Table 5 (gyroscope values) and Table 6 (heart rate values) respectively

TABLE 4

(accelerometer data used as training dataset for training the system 100)

| acc_meanx | acc_sdx | acc_meany | acc_sdy | acc_meanz | acc_sdz |
|---|---|---|---|---|---|
| 0.526517659 | 0.162992467 | −5.33413835 | 0.710949421 | 8.517941008 | 0.420529712 |
| 4.681956284 | 0.55424362 | −7.400299424 | 0.426986549 | 4.835628644 | 0.907603423 |
| 0.555690758 | 0.066502424 | −4.617712623 | 0.163411852 | 9.035636642 | 0.087199308 |
| −0.043795899 | 1.019587822 | −3.029313464 | 1.263667611 | 9.563894503 | 0.605747889 |
| ... | ... | ... | ... | ... | ... |
| 0.545539392 | 0.152354812 | −5.279315973 | 0.574596351 | 8.61413723 | 0.34753517 |
| 0.062527597 | 0.129872564 | −5.947469451 | 0.225323288 | 8.198704551 | 0.146185911 |

TABLE 5

(gyroscope data used as training dataset for training the system 100)

| gy_meanx | gy_sdx | gy_meany | gy_sdy | gy_meanz | gy_sdz |
|---|---|---|---|---|---|
| 1.197700008 | 4.777569471 | −0.458500003 | 1.109331951 | −0.458500003 | 1.51741451 |
| 1.518299991 | 8.380562444 | 1.420300012 | 3.422951285 | 1.420300012 | 7.737285281 |
| 0.423500009 | 2.487953598 | −0.319900001 | 1.196672439 | −0.319900001 | 1.763284708 |
| 0.833699942 | 16.23398559 | 4.331600004 | 9.994648456 | 4.331600004 | 16.70408377 |
| ... | ... | ... | ... | ... | ... |
| 1.747900029 | 8.12663205 | −0.138600001 | 2.394089566 | −0.138600001 | 2.719173084 |
| −0.067899982 | 5.063032394 | 0.1113 | 1.127298871 | 0.1113 | 1.714388337 |

TABLE 6

(heart rate data used as training dataset for training the system 100)

| meanhr | sdhr |
|---|---|
| 81.43 | 1.36568664 |
| 72.82 | 1.013706072 |
| 70.35 | 0.476969601 |
| 86.41 | 1.049714247 |
| ... | ... |
| 75.82 | 0.792212093 |
| 83.9 | 1.3 |

In a wearable device scenario, there are many sensors. In the present disclosure, the system 100 used data from accelerometer, heart rate and gyroscope as input(s). Accelerometer is used to determine the orientation and movement of the person wearing the smartwatch (or any wearable device or a computing device that is capable of providing accelerometer, heart rate and gyroscope data). A heart rate is present in the smartwatch that sense the heart rate variations of the person wearing the smartwatch. A gyroscope is present in the smartwatch to sense angular rotational velocity and acceleration. Accelerometer and Gyroscope provide a in 3 dimensions through x, y and z axis. The heart rate is provided as one dimension. The accelerometer, and gyroscope data are normally providing a large set of values in the above x, y, and z axis in a very short span. (though a configurable parameter) and so is the heart rate. Evaluating these values and applying as input to machine learning features is subject to lot of variations and large computation. To effectively manage this, mean and standard deviation of data from accelerometer and gyroscope sensors in x, y and z axis plus the heart rate data was utilized by the system 100 of the present disclosure for fundamental reasons. Mean takes into account all the values i.e., in x, y and z axis in the distribution of accelerometer and gyroscope values plus single dimension values in the heart rate and it further provides a central tendency is a single value that attempts to describe a set of data by identifying the central position with that data. Standard Deviation is another best measure of variation in a typical distribution. It is based on every item/data value in the distribution of accelerometer, heart rate and gyroscope values and it is less affected by fluctuations of distribution.

Therefore, using mean and average of values i.e., in x, y and z axis in the distribution of accelerometer and gyroscope values and single dimension values in heart rate gave more stability from data standpoint and the accuracy of the prediction could be arrived with a straight forward classifiers such as random forest (RF)/support vector machine (SVM) rather going for one or more neural network(s) such as Long Short Term Memory (LSTM) network(s).

Along with the above features, activity label for each corresponding feature is also collected. For instance, in this case, the activity label may comprise corresponding labels as [0, 0, 0, 0, . . . , 0, 0]. Below is an illustrative pseudo code for extraction of accelerometer, heart rate and gyroscope features from dataset:

FeaturedDataset=Featureextraction (Aclgyrohrdataxyz)

FeatureDataset is unified dataset obtained from Featureextracton function applied on x, y, z vectors of Accelerometer and Gyroscope data plus on the single dimension values in heart rate data which is represented in variable "Aclgyrohrdataxyz"

Once the above features are detected and extracted, the obtained set of features are pre-processed to obtain a pre-processed feature set. The pre-processed feature set is split into training feature set and test feature set. In other words, once the features are extracted, compiled and labels are assigned, the next step is to split the entire dataset into training and test dataset. In the present disclosure, the training and test dataset were split with a ratio of 85 and 15 respectively, i.e., 85% serves as training dataset and 15% serves as test dataset. Below is an illustrative pseudo code for the above splitting:

TrainActivity, TestActivity, Trainlabel,
  Testlabel=TrainTestSplit (FeaturedDataset)

TrainActivity: represents training data which has x, y, z vectors of accelerometer and gyroscope and single dimensional vector of heart rate TestActivity: represents testing data which has x, y, z vectors of accelerometer and gyroscope and single dimensional vector of heart rate Trainlabel: represents training label for the activity.

Testlabel: represents testing label for the activity

From the label aspect, "0" represents Eating, "1" represents Walking and "2" represents "Normal".

Once the featured dataset has been split into Training and Test dataset, an activity prediction model is created. The training data and training labels are fed to a classifier (e.g., the Random Forest Classifier), wherein objective is to derive the activity prediction model with fitment to training dataset and training label. Below is an illustrative pseudo code for generating the activity prediction model:

ActivityPredictionModel=RandomForestAlgorithm
  (TrainingData, TrainingLabel)

Once the activity prediction model is created, accuracy of this model is checked by feeding predicting with Test dataset.

PredictedActivity=ActivityPredictionModel.predict
  (TestData)

Based on the predicted Activity, the performance measures of the activity prediction model such as accuracy, precision, recall, and F1-score are derived. In this Activity Detection model, the F1 score is considered as the primary measure of the performance by the system 100 of the present disclosure. In other words, the activity detection model is generated using a classifier (e.g., Random Forest classifier) based on a set of training features obtained from the pre-processed feature set and the activity detection model is applied on a remaining set of features serving as a set of test features obtained from the pre-processed features set to determine an accuracy of activity prediction. Below is an illustrative test feature set of (i) mean and standard deviation of accelerometer data (AD) values in Table 7, (ii) mean and standard deviation of gyroscope data (GD) values in Table 8, and mean and standard deviation of heart rate data (HRD) values in Table 9 wherein the Activity Detection model was applied on the test feature set.

TABLE 7

| acc_meanx | acc_sdx | acc_meany | acc_ady | acc_meanz | acc_sdz |
|---|---|---|---|---|---|
| −2.55628383 | 1.552541734 | −7.440204028 | 2.604932852 | 4.81380319 | 2.865599818 |
| −2.616636137 | 2.417729628 | −8.652349996 | 3.068062908 | 0.014066881 | 2.338354472 |
| 3.325660917 | 2.751573497 | −7.04229456 | 4.463237491 | 2.367299204 | 3.489269056 |
| −2.593868075 | 2.094911723 | −7.09546831 | 2.971479101 | −0.669724442 | 5.522896979 |
| −3.648740301 | 2.135647462 | −7.09650767 | 2.473214309 | −2.357437855 | 4.681588731 |
| −2.381535274 | 1.857888187 | −8.92858808 | 2.322274683 | −0.644998645 | 2.910689588 |

TABLE 8

| gy_meanx | gy_sdx | gy_meany | gy_sdy | gy_meanz | gy_sdz |
|---|---|---|---|---|---|
| 5.168100074 | 48.52743578 | 2.044700129 | 16.93314778 | 2.044700129 | 32.87438266 |
| 2.977800029 | 23.14129182 | 1.87109981 | 30.62041763 | 1.871099981 | 55.26965798 |
| 0.434000189 | 45.78596519 | −3.459400122 | 61.77111266 | −3.459400122 | 74.18509036 |
| 2.510200115 | 63.85232318 | −0.40809992 | 64.98121105 | −0.408099924 | 46.16643869 |
| 1.976100214 | 44.86476595 | 2.460499977 | 73.57060307 | 2.460499977 | 48.03023127 |
| 1.455299944 | 27.97128251 | −6.154399897 | 51.31952139 | −6.154399897 | 41.92024535 |

TABLE 9

| Meanhr | sdhr |
|---|---|
| 75.28 | 1.03033975 |
| 88.29 | 0.5156549229 |
| 75.77 | 0.705053189 |
| 68.81 | 0.643350604 |
| ... | ... |
| 81.73 | 2.340320491 |
| 70.09 | 0.28618176 |

A confusion matrix was outputted by the system 100, wherein out of the given training dataset of accelerometer, heart rate and gyroscope values of subjects, 142 were detected/identified as non-eating activities, 19 were detected/identified as eating activities and served as true positives and 2 were detected/identified as false positives (wherein actual eating activities were identified as non-eating).

Based on the above results, during the training of the system 100, the activity prediction model was then fine-tuned and optimized till the F1 score exceeded a pre-defined threshold, say in this case the pre-defined threshold was set as 0.9.

Figure 3A:
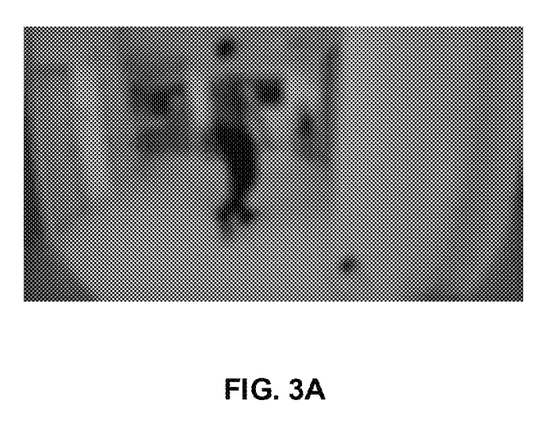
FIG. 3A depicts a training video data capturing an activity performed by a user, in accordance with an embodiment of the present disclosure.
Figure 3B:
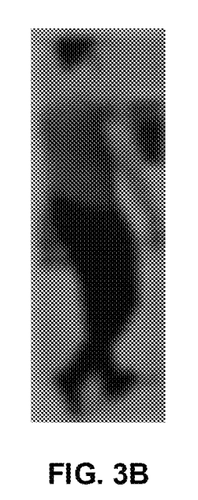
FIG. 3B depicts a resized bounding box of the user comprised in a frame of the training video data capturing the activity performed by the user, in accordance with an embodiment of the present disclosure.
Figure 3C:
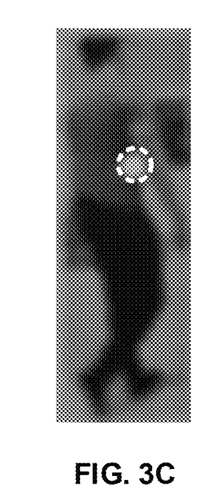
FIG. 3C depicts a training pose coordinate in a resized bounding box of the user, in accordance with an embodiment of the present disclosure.

As mentioned above and described the way training dataset was collected for activity prediction model generation, training video data was also collected for activity detection and validation. For instance, training video data is captured from the image capturing device wherein the training video data comprises information specific to one or more users. An activity label is tagged for each activity identified in one or more frames comprised in the training video data. Each of the one or more frames comprised in the training video data is then processed to extract a bounding box of the one or more users and one or more training vectors of pose coordinates are generated using the bounding box of the one or more users (e.g., bounding box upon being resized). For instance, FIG. 3A, with reference to FIGS. 1 through 2, depicts a training video data capturing an activity performed by a user, in accordance with an embodiment of the present disclosure. FIG. 3B, with reference to FIGS. 1 through 3C, depicts a resized bounding box of the user comprised in a frame of the training video data capturing the activity performed by the user, in accordance with an embodiment of the present disclosure. To effectively identify an activity of interest that is captured in Training dataset against the real video, it is very critical to understand the activity of the person without any noise. Without any noise means in this context, only user is to be captured leaving all the background. So, it is very important to extract the person activity only as a bounded box. For example, as presented in the FIG. 3B. FIG. 3C, with reference to FIGS. 1 through 3B, depicts a training pose coordinate in the resized bounding box of the user, in accordance with an embodiment of the present disclosure. More specifically, the training pose point is depicted and indicative by way of a white dot or white circle, in an embodiment of the present disclosure. The above examples depicted in FIGS. 3A through 3C are better understood by way of following explanation and shall not be construed as limiting the scope of the present disclosure.

The creation of the bounded box is done both on training dataset of images and test set of images. The important aspect here is, the bounding box is created only if there exists a "Person/user" in that image. If there are no "Person", then that image is discarded from usage. This applies to both frames from training and real video images. By doing this, one or more noise of "Non-Person" images are eliminated. The other reason performing this step is very essential in improving the accuracy of detecting activities irrespective of difference in training and real video frame images. For the bounded box, YOLO (stands for You Only Look Once) cafe library components implemented through Python program (and as known in the art) was utilized by the system 100 of the present disclosure. An illustrative pseudo code is given below:

```
createboundedbox(image):
{
    boundedbox = image[startY:endY,startX:endX]
}
```

Once the bounded box activity is performed, next step is to ensure image resizing of the bounded box image. Objective of this resizing exercise is to ensure greater accuracy. Resizing of the bounded box resize ensures the training image resize is twice the size of the real video frame images. The resizing of the training and real video images varies based on the frame width of the real video (e.g., in other words, specification of each frame in a video data, be it training video data or an incoming live video feed). For example, if the video frame image comes with frame width of 320, the training set resizing tends to be 4.0 of the original size and real video frame image tends to be 2.0 of the original image. Main purpose of the resizing is to ensure proper human pose points (or pose coordinates) are obtained from both training images and live video frames.

Once the bounding box of the person is detected and resized, the next important step is to understand key points (or pose coordinates) in the person body or rather put it simply the human body. In this context, Human POSE estimation concept has been utilized/implemented by the system 100 of the present disclosure. The important objective of Human POSE estimation is to detect key point locations of a Human body (also referred as pose coordinates). The human body key points in this context is to find detect and localize the major parts/joints of the body e.g., head, shoulder, neck, etc. For the Human POSE estimation, the system 100 has extensively used pretrained Multi Person Dataset (MPII) models trained on Caffe Deep Learning Framework in opencv. Below is an illustrative pseudo code for pose coordinates estimation:

```
PoseEstimation (image):
{
    PoseBodyPoints = image[startY:endY,startX:endX]
}
```

An overall pseudo code for activity detection from training video data is provided by way of following non-construing example:
For each TrainingImage in TrainingSetImages TrainingImage=boundedbox (TrainingImage]

TrainingImage=imgresize (TrainingImage, "trainvideo")

TrainingPOSEPoints=PoseEstimation (TrainingImage)

Array (TrainingSet[i,j]=TrainingImage[i], TrainingActivity[j])

Below are illustrative examples of one or more training vector of pose coordinates as generated and stored in the memory 102 of the present disclosure:
1. Training vector of pose coordinates for sitting activity 1 is as follows:
   [47, 71, 42, 58, 42, 58, 35, 66, 42, 61, 42, 58, 42, 58, 42, 61, 34, 71, 42, 58, 42, 58, 32, 68, 42, 58, 42, 58]
2. Training vector of pose coordinates for sitting activity 2 is as follows:
   [48, 71, 42, 58, 42, 58, 35, 66, 42, 61, 42, 58, 42, 58, 44, 61, 35, 68, 42, 61, 42, 58, 34, 66, 42, 58, 42, 58]
3. Training vector of pose coordinates for sitting activity 3 is as follows:
   [35, 67, 42, 64, 44, 59, 48, 51, 44, 62, 42, 64, 50, 53, 31, 70, 42, 70, 42, 67, 42, 64, 42, 70, 33, 70, 42, 64]
4. Training vector of pose coordinates for walking activity 1 is as follows:
   [46, 71, 52, 71, 52, 71, 44, 87, 44, 87, 50, 71, 9, 126, 57, 65, 54, 98, 52, 93, 48, 87, 54, 98, 50, 71, 48, 87]
5. Training vector of pose coordinates for walking activity 2 is as follows:
   [56, 148, 58, 131, 54, 136, 38, 91, 38, 85, 43, 113, 29, 91, 36, 85, 36, 79, 18, 74, 25, 102, 36, 79, 27, 91, 27, 96]
6. Training vector of pose coordinates for walking activity 3 is as follows:
   [42, 142, 33, 132, 33, 137, 39, 151, 39, 151, 35, 137, 39, 146, 37, 142, 37, 132, 39, 127, 35, 142, 39, 132, 39, 127, 35, 142]
7. Training vector of pose coordinates for walking activity 4 is as follows:
   [47, 46, 40, 79, 31, 83, 29, 116, 32, 116, 29, 97, 38, 139, 40, 102, 32, 134, 49, 107, 40, 144, 38, 97, 42, 148, 40, 148]

Referring to steps of FIG. 2, once the input data comprising (i) the accelerometer data, the heart rate and the gyroscope data from the wearable device associated with the user, (ii) the video data captured from the image capturing device, the video data comprising information associated with the user, is obtained, at step 204, the one or more hardware processors 104 detect a first activity of the user from each of the accelerometer data, the heart rate data and the gyroscope data obtained from the wearable device associated with the user by: extracting a plurality of features from the accelerometer data, heart rate data and the gyroscope data and pre-processing thereof to obtain a set of pre-processed features; and detect, via the activity detection model, the first activity being performed by the user, using the set of pre-processed features. At step 206, the one or more hardware processors 104 detect a second activity of the user from the video data captured from the image capturing device. It is to be understood by a person having ordinary skill in the art or the person skilled in the art that steps 204 and 206 can either be performed in a sequential manner or be performed in parallel, depending upon the order of (i) the accelerometer data, the heart rate data and the gyroscope data from the wearable device associated with the user, (ii) the video data captured from an image capturing device. Both (i) the accelerometer data, the heart rate data and the gyroscope data from the wearable device associated with the user, (ii) the video data captured from an image capturing device may be fed as an input simultaneously, in one example embodiment. Accelerometer data, heart rate data and gyroscope data from the wearable device associated with the user may be first fed to the system 100 and processed for activity detection, followed by the video data captured from an image capturing device, in another example embodiment. the video data captured from an image capturing device may be first fed to the system 100 and processed for activity detection followed by the accelerometer data, heart rate data and gyroscope data from the wearable device associated with the user, in yet another example embodiment.

More specifically, the first activity is detected by extracting a plurality of features from the accelerometer data, heart rate data and the gyroscope data and pre-processing thereof to obtain a set of pre-processed features; and detecting, via the activity detection model executed by the one or more hardware processors, the first activity being performed by the user, using the set of pre-processed features. As described in the training approach, the system 100 follows the same methodology for an incoming raw data (e.g., accelerometer, heart rate and gyroscope data of the user).

Figure 4A:
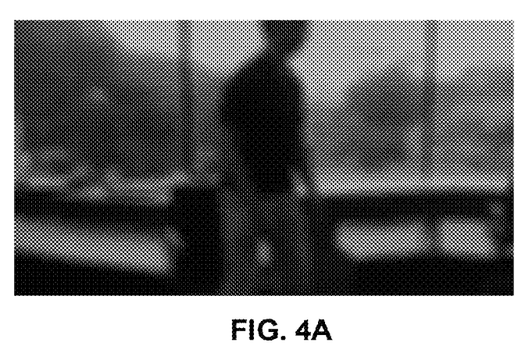
FIG. 4A depicts an image from a frame comprised in a video data obtained by the system of FIG. 1, in accordance with an embodiment of the present disclosure.
Figure 4B:
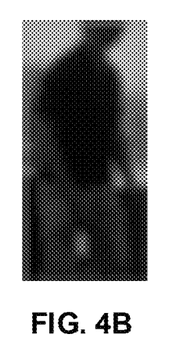
FIG. 4B depicts an image with a resized bounding box of the user present in the frame comprised in the video data obtained by the system of FIG. 1, in accordance with an embodiment of the present disclosure.
Figure 4C:
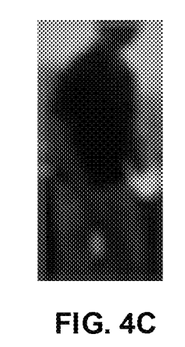
FIG. 4C depicts an image with a vector of pose coordinates of the user, being estimated in the frame comprised in the video data obtained by the system of FIG. 1, in accordance with an embodiment of the present disclosure.

The second activity is detected by: processing each frame from the video data to extract a bounding box of the user; resizing the bounding box of the user to obtain a resized bounding box; detecting and extracting a vector of pose coordinates from the resized bounding box; computing, via a Chebyshev Distance technique, a Chebyshev distance between (i) the vector of pose coordinates and (ii) one or more training vectors of pose coordinates stored in a database to obtain a plurality of distances; and detecting the second activity based on the plurality of computed distances. FIG. 4A, with reference to FIGS. 1 through 3C, depicts an image from a frame comprised in the video data obtained by the system 100 of FIG. 1, in accordance with an embodiment of the present disclosure. FIG. 4B, with reference to FIGS. 1 through 4A, depicts an image with a resized bounding box of the user present in the frame comprised in the video data obtained by the system 100 of FIG. 1, in accordance with an embodiment of the present disclosure. FIG. 4C, with reference to FIGS. 1 through 4A, depicts an image with a vector of pose coordinates of the user, being estimated in the frame comprised in the video data obtained by the system 100 of FIG. 1, in accordance with an embodiment of the present disclosure. For instance, based on the extracted bounding box of the user, the resized bounding box, a vector of pose coordinates is estimated/generated by the system 100. The vector of pose coordinates is provided by way of an illustrative example below:

[40, 116, 27, 116, 27, 112, 40, 123, 20, 98, 27, 105, 41, 123, 20, 94, 26, 116, 29, 108, 69, 108, 26, 105, 27, 105, 69, 105]

One or more training vectors of pose coordinates are obtained from the memory 102 of the system 100 and a distance is computed for (i) the vector of pose coordinates of the user captured (refer FIGS. 4A through 4C) and (ii) the one or more training vectors of pose coordinates. Assuming, distance of (i) the one or more training vectors of pose coordinates and (ii) the vector of pose coordinates of the input video data as below:

[[65, 'Sitting'], [65, 'Sitting'], [72, 'Sitting'], [45, 'Walking'], [44, 'Walking'], [53, 'Walking'], [70, 'Walking']]

In the above example, [65, "sitting"] refers the distance between Sitting training pose coordinate vector and the vector of pose coordinate of the live frame/input video. In other words, there are a set of distances obtained, one distance computed for each pose coordinate. A comparison of each computed distance across the plurality of computed distances is performed by the system 100. In this case, say distance of pose coordinate is compared with other distances for detecting the second activity. In other words, based on the distance computed, it can be observed that the distance 'pose coordinate '[44]' serving as a distance of a pose coordinate has the best minimal distance amongst other distances of other pose coordinates when compared to a corresponding distance of a training pose coordinate '[45]'. Therefore, as per the distance of training vector pose coordinate [44, 'Walking'], the second activity is detected as a 'walking activity'. Below is an illustrative pseudo code for detecting an activity of the user from the video data:

VideoData=LoadVideoFile ("Example.mp4")

For each VideoFrame in VideoData

VideoFrame=BoundedBox (Videoframe)

VideoFrame=imgresize (Videoframe, "realvideo")

Live VideoPOSEPoints=PoseEstimation (VideoFrame)

PerformDistanceCalculation (Live VideoPOSEPoints, TrainingSet, Threshold)

As can be observed from last 3 lines of the above pseudo code, there is a function PerformDistanceCalculation( ). This is going to be another important function which is going perform the critical Activity Detection logic based on the activity present in Posepoints (also referred as pose coordinates of an incoming video data) of a VideoFrame array along with the Array of Training set Posepoints Data (also referred as training vector of pose coordinates). Following are the parameters that are fed as input to PerformDistanceCalculation.

1. POSE Points/pose coordinates of the live video frame for a person/user
2. TrainingSet Array which comprises both TrainingsetImagePosepoints along with TrainingActivity label
3. Threshold value to be compared.

Distance Calculation is the last step of PerformDistanceCalculation function which forms critical process of determining distances between Training Set Posepoints which constitutes various Activity of Interest like Sitting/Walking etc. with Live video frame PosePoints. So fundamentally every row in the Training set array contains the following:

1. Vector of points that identify human poses which is obtained from TrainingActivity image such as Sitting, Walking, and the like.
2. Activity Label of the Training Image.

In the same way, every record in the live video frame contains a Vector of human pose coordinates. As part of distance calculation function, every input training pose points and live video frame pose points are calculated through Chebyshev Distance formula method as known in the art. Chebyshev distance (or Tchebyshev distance) is a metric defined on a vector space where the distance between two vectors is the greatest of their differences along any coordinate dimension.

The objective of using Chebyshev distance function is to find the minimum distance between training pose points and live video frame pose points. For instance, for example, if the Chebyshev distance between training pose points of a Sitting activity and live video pose points is less compared to training pose points of a Standing activity and live video pose points, then activity is detected as "Sitting" and threshold value is set to distance that is obtained from training pose points of Sitting activity with live video frame activity. Fundamentally, the lesser the Chebyshev distance between the training pose points and live video frame is taken into consideration, a specific activity is deemed to be an actual determined activity.

Below is an illustrative pseudo code for the above explanation/analysis:

PerformDistanceCalculation (LiveVideoPOSEPoints, TrainingSet, Threshold)

For InputTrainingPosePoints in TrainingSet:

mythreshold = dist.chebyshev[InputTrainingPosePoints [0][0]],         LiveVideoPOSEPoints)

if mythreshold < getthresholdvalue:

getthresholdvalue = mythreshold             getactivityname = InputTrainingPosePoints [1]

Distances which match the thresholds or below thresholds which determines the Activity of Interest once the match/AOI is found, that activity is recorded by the system 100. This process is repeated for all live video frame pose points, so that training pose point sets is scanned against the entire frame set of the video. The objective of using Chebyshev distance function is after lot of iterations, trying out different distance formulas like Manhattan distance, Cosine distances, Euclidean distances, the accuracy obtained from Chebyshev function seems to be much higher.

As mentioned above, variety of distance measures along with Chebyshev distance such as cosine distance, Manhattan and Euclidean distances were tried during experiments/testing. Now, during the activity recognition of training video and live/input video validation in identical background with a single user, most of the distance calculations worked out decently with x % accuracy (e.g., say 90% accuracy). However, when the training environment i.e., video was taken in one background with different user and live environment which is a video taken in different background even with different user, the Manhattan, Euclidean distances and cosine distance came out with very less accuracy less than y % (e.g., 30%). Similar testing was done with Chebyshev distance, and it was observed that the accuracy reached around 90% plus. Hence, the experimental results described in the present disclosure related to use of Chebyshev distance technique implementation because of this robustness even while working across multiple backgrounds. It is to be understood by a person having ordinary skill in the art or person skill in the art that with further research and work around, other distance computation techniques can be implemented for increase in accuracy and such examples shall not be construed as limiting the scope of the present disclosure.

At step 208 of the present disclosure, upon detecting the first activity and the second activity, the one or more hardware processors 104 validate the first activity and the second activity based on a comparison of (i) the first activity predicted based on the accelerometer data, the heart rate data and the gyroscope data from the wearable device associated with the user and an associated timestamp (e.g., a timestamp at which the first activity was performed) and (ii) the second activity predicted based on the video data captured from the image capturing device and an associated timestamp (e.g., a timestamp at which the second activity was performed), to obtain a true positive or a false positive. In an embodiment of the present disclosure, the true positive indicates that the first activity and the second activity are identical. In another embodiment, the false positive indicates that the first activity and the second activity are different from each other. For instance, in case the validation results as a true positive, it can be inferred as activity detected from both (i) accelerometer, heart rate and gyroscope data and (ii) video data is of the same type at a given timestamp (e.g., in this case walking). In case the validation results as a false positive, it can be inferred as activity detected from the accelerometer, the heart rate and gyroscope data is of the type say sitting and activity detected from the video data is of another type (e.g., non-sitting activity such as standing, walking, and the like).

The system 100 of the present disclosure ensures that the activity that is predicted through smartwatch and videoframe are crosschecked and validated. By performing validation, the system 100 ensures the activity prediction and increase in the accuracy of the prediction. Assuming activity predicted through the smartwatch and video frames in the "ActivityStore" table are comprised in the memory 102 of the system 100. The 'activitystore' table has 3 attributes i.e., Date-Time, Activity and ActivitySource as shown in the below Table 5.

TABLE 5

| Date and timestamp | Activity | Activity source |
|---|---|---|
| 11/25/2019 13:11:00 PM | Walking | Video |
| 11/25/2019 13:11:00 PM | Walking | Smartwatch |
| 11/25/2019 13:12:00 PM | Walking | Video |
| 11/25/2019 13:12:00 PM | Walking | Smartwatch |

As part of the validation, based on the specific date and time as a user-initiated query, the "ActivityStore" table comprised in the memory 102 is queried for a specific activity for a given date and time up to minute. Based on the query, the activities are retrieved and checked. In the above sample if the query is initiated for afternoon 11'o clock on November 25th, it may be observed that the user indeed performed walking activity as validated by the different Activitysource (e.g., activity detection as per step 204 and 206 respectively). It is to be understood by a person having ordinary skill in the art or person skilled in the art that FIGS. 3A through 4C are blurred accounting for privacy issues of a user and the present disclosure provides systems and methods which involve activity detection and validation from the images/frames captured and extracted from the video data.

As mentioned above, elderly population is steadily increasing in most countries due to a decline in birth and mortality rate. The population of independently living senior citizens has also become significant. This has led to an active research focus in geriatric wellness. Apart from the usual physical and cognitive decline that proceeds with age, there are much softer aspects such as dignity and ability to live independently (age-in-place). If subjects are monitored all the time by instrumenting them heavily, technology can possibly predict and prevent many abnormal situations. In today's environment, most of the activity detection i.e., walking, eating, typing the keyboard etc. takes place through wearable device/smartwatches and the like. Performing the activity detection only through one mode i.e., smart watch, though it works in reasonable cases, however there are chances of false positives considerably. There are other approaches such as surveillance. However, such approaches are limited to object detection.

Based on the challenges mentioned in the above section, the present disclosure provides a system (e.g., the system 100) that implements a method as described in FIG. 2 for detecting activities being performed by users with reasonable accuracy, thereby providing a proactive mode for care-givers to take care of users (e.g., specifically elderly population living in Assisted Living Homes). In the present disclosure, an activity detection is performed by the system 100 through multi-fold monitoring methodologies (e.g., multiple sensors wherein accelerometer, heart rate and gyroscope data are acquired from one source and video data is obtained likewise) thereby reducing dependency of single methodology-based activity detection. Further, the system 100 performs validation of activities detected from the above approaches to determine whether activity indeed happened or not after the detection of activities by smartwatch and video which are indicative of true positive or false positive. The overall activity detection involving smartwatch and video is done through unique combination of machine learning and deep learning techniques that helps in gaining considerable accuracy as mentioned above.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for activities detection and validation of the activities detection, comprising:

obtaining, via one or more hardware processors, (i) accelerometer data, heart rate data, and gyroscope data from a wearable device associated with a user, (ii) video data captured from an image capturing device, wherein the video data comprises information associated with the user;

obtaining, via the one or more hardware processors, mean values and standard deviation values of the accelerometer data, the heart rate data, and the gyroscope data, wherein the mean values and the standard deviations values are obtained by performing operations on each of the accelerometer data, the heart rate data, and the gyroscope data;

detecting, via the one or more hardware processors, a first activity of the user from each of the mean values and the standard deviations values of each of the accelerometer data, the heart rate data, and the gyroscope data by:

extracting, via the one or more hardware processors, a plurality of features from each of the mean values and the standard deviations values of the accelerometer data, the heart rate data, and the gyroscope data; and pre-processing the plurality of features to obtain a set of pre-processed features;

splitting the set of pre-processed features into a training feature set and a test feature set;

detecting, via an activity detection model executed by the one or more hardware processors, the first activity being performed by the user, wherein the activity detection model is generated using a Random Forest classifier based on the training feature set, and the activity detection model is applied on the test feature set to determine an accuracy of activity prediction;

detecting, via the one or more hardware processors, a second activity of the user from the video data captured from the image capturing device by:

processing, via one or more hardware processors, each frame of the video data to extract a bounding box around an image of the user, wherein the bounding box is a first specific image obtained from each frame of the video data, wherein the first specific image is obtained from each frame by:
    retaining the image of the user in each frame of the video, and
    removing background noise in each frame of the video data; and
an activity label is tagged for each activity identified in each frame of the video data;
resizing, the one or more hardware processors, the first specific image to obtain a second specific image, wherein a size of the second specific image is double of a size of each frame of the video data;
detecting and extracting, via the one or more hardware processors, one or more vector of pose coordinates from the second specific image, wherein the vector of pose coordinates corresponds to a plurality of joints of a body of the user in the second specific image;
computing, via a Chebyshev Distance technique executed by the one or more hardware processors, a distance between (i) the detected one or more vector of pose coordinates and (ii) one or more predefined training vectors of pose coordinates to obtain a plurality of distances, wherein
    each distance of the obtained plurality of distances corresponds to each pose coordinate of the one or more pose coordinates, and
    the one or more predefined training vectors of pose coordinates are based on:
        (i) vector points that identify human poses of a test user which is obtained from a plurality of training activity images, wherein the plurality of training activity images includes at least one of sitting image, a walking image, walking image, and
        (ii) a specific activity label of the plurality of training activity images; and
determining a minimum distance among the obtained plurality of distances;
detecting, via the one or more hardware processors, the second activity based on the determined minimum distance; and
validating, via the one or more hardware processors, the first activity and the second activity based on a comparison of:
    (i) the detected first activity using the activity detection model with an associated timestamp at which the first activity is recorded, and
    (ii) the detected second activity based on the determined minimum distance with the associated timestamp at which the second activity is recorded;
obtaining a false positive result related to the first activity and the second activity based on comparison of:
    the detected first activity using the activity detection model, and
    the detected second activity based on the determined minimum distance, wherein false positive result indicates that:
        the first activity is different from the second activity, and
        one of the first activity or the second activity is not deemed to have occurred at the associated timestamp.

2. The processor implemented method as claimed in claim 1, further comprising obtaining the second specific image based on a specification of each frame of the video data.

3. The processor implemented method as claimed in claim 1, wherein the one or more predefined training vectors of pose coordinates are obtained by:
    obtaining, via the one or more hardware processors, training video data that is captured from a specific image capturing device, wherein the training video data comprises specific information specific to one or more specific users, wherein the one or more specific user are different from the user;
    tagging, via the one or more hardware processors, an activity label for each activity identified in one or more frames of the training video data;
    processing, via the one or more hardware processors, each of the one or more frames of the training video data to extract a training image of the one or more users; and
    generating, via the one or more hardware processors, the one or more predefined training vectors of pose coordinates using the training image of the one or more specific users.

4. The processor implemented method as claimed in claim 1, further comprises:
    performing, via the one or more hardware processors, a comparison of each computed distance across the plurality of computed distances; and
    detecting, via the one or more hardware processors, the second activity based on the comparison.

5. The processor implemented method as claimed in claim 1, wherein a true positive result associated with the first activity and the second activity indicates that the first activity and the second activity are identical.

6. A system, comprising:
    a memory storing instructions;
    one or more communication interfaces; and
    one or more hardware processors coupled to the memory via the one or more communication interfaces, wherein the one or more hardware processors are configured by the instructions to:
        obtain (i) accelerometer data, heart rate data, and gyroscope data from a wearable device associated with a user, (ii) video data captured from an image capturing device, wherein the video data information associated with the user;
        obtain mean values and standard deviation values of the accelerometer data, the heart rate data, and the gyroscope data, wherein the mean values and the standard deviations values are obtained by performing operations on each of the accelerometer data, the heart rate data, and the gyroscope data;
        detect a first activity of the user from each of the mean values and the standard deviations values of each of the accelerometer data, the heart rate data, and the gyroscope data by:
            extracting a plurality of features from each of the mean values and the standard deviations values of the accelerometer data, the heart rate data, and the gyroscope data; and
            pre-processing the plurality of features thereof to obtain a set of pre-processed features;
            splitting the set of pre-processed features into a training feature set and a test feature set;
            detecting, via an activity detection model executed by one or the more hardware processors, the first activity being performed by the user, wherein the activity detection model is generated using a Random Forest classifier based on the training feature set, and the activity detection model is applied on the test feature set to determine an accuracy of activity prediction;

detect a second activity of the user from the video data captured from the image capturing device by:

processing each frame of the video data to extract a bounding box around an image the user, wherein the bounding box is a first specific image obtained from each frame of the video data, wherein the first specific image is obtained from each frame by:

retaining the image of the user in each frame of the video, and removing background noise in each frame of the video data; and an activity label is tagged for each activity identified in each frame of the video data;

resizing the first specific image bounding box of the user to obtain a second specific image, wherein a size of the second specific image is double of a size of each frame of the video data;

detecting and extracting one or more vector of pose coordinates from the second specific image, wherein the vector of pose coordinates corresponds to a plurality of joints of a body of the user in the second specific image;

computing, via a Chebyshev Distance technique executed by the one or the more hardware processors, a distance between (i) the detected one or more vector of pose coordinates and (ii) one or more predefined training vectors of pose coordinates to obtain a plurality of distances, wherein each distance of the obtained plurality of distances corresponds to each pose coordinate of the one or more pose coordinates, and the one or more predefined training vectors of pose coordinates are based on:

(i) vector points that identify human poses of a test user which is obtained from a plurality of training activity images, wherein the plurality of training activity images includes at least one of sitting image, a walking image, walking image, and (ii) a specific activity label of the plurality of training activity images; and determining a minimum distance among the obtained plurality of distances; and detecting the second activity based on determined minimum distance; and validate the first activity and the second activity based on a comparison of:

(i) the detected first activity using the activity detection model with an associated timestamp at which the first activity is recorded, and (ii) the detected second activity based on the based on the determined minimum distance with the associated timestamp at which the second activity is recorded;

obtain a false positive result related to the first activity and the second activity based on comparison of:

the detected first activity using the activity detection model, and the detected second activity based on the based on the determined minimum distance, wherein false positive result indicates that:

the first activity is different from the second activity, and one of the first activity or the second activity is not deemed to have occurred at the associated timestamp.

7. The system as claimed in claim 6, wherein the one or more hardware processors are further configured to obtaining the second specific image based on a specification of each frame comprised in of the video data.

8. The system as claimed in claim 6, wherein the one or more predefined training vectors of pose coordinates are obtained by:

obtaining training video data that is captured from a specific image capturing device, wherein the training video data comprises specific information specific to one or more specific users, wherein the one or more specific user are different from the user;

tagging an activity label for each activity identified in one or more frames of the training video data;

processing each of the one or more frames of the training video data to extract training image of the one or more users; and generating the one or more predefined training vectors of pose coordinates using the training image of the one or more specific users.

9. The system as claimed in claim 6, wherein the one or more hardware processors are further configured to:

perform a comparison of each computed distance across the plurality of computed distances; and detect the second activity based on the comparison.

10. The system as claimed in claim 6, wherein a true positive result associated with the first activity and the second activity indicates that the first activity and the second activity are identical.

11. A computer program product comprising a non-transitory computer readable medium having a computer readable program embodied therein, wherein the computer readable program, when executed on a computing device, causes the computing device to detect activities and validate the activities by:

obtaining, via one or more hardware processors of the computing device, (i) accelerometer data, heart rate data, and gyroscope data from a wearable device associated with a user, (ii) video data captured from an image capturing device, wherein the video data comprises information associated with the user;

obtaining, via the one or more hardware processors, mean values and standard deviation values of the accelerometer data, the heart rate data, and the gyroscope data, wherein the mean values and the standard deviations values are obtained by performing operations on each of the accelerometer data, the heart rate data, and the gyroscope data;

detecting, via the one or more hardware processors, a first activity of the user from each of the mean values and the standard deviations values of each of the accelerometer data, the heart rate data, and the gyroscope data by:

extracting a plurality of features from each of the mean values and the standard deviations values of the accelerometer data, the heart rate data and the gyroscope data; and pre-processing the plurality of features to obtain a set of pre-processed features;

splitting the set of pre-processed features into a training feature set and a test feature set;

detecting, via an activity detection model executed by the one or more hardware processors, the first activity being performed by the user, wherein
the activity detection model is generated using a Random Forest classifier based on the training feature set, and
the activity detection model is applied on the test feature set to determine an accuracy of activity prediction;

detecting, via the one or more hardware processors, a second activity of the user from the video data captured from the image capturing device by:
processing each frame of the video data to extract a bounding box around an image of the user, wherein
the bounding box is a first specific image obtained from each frame of the video data, wherein the first specific image is obtained from each frame by:
retaining the image of the user in each frame of the video, and
removing background noise in each frame of the video data; and
an activity label is tagged for each activity identified in each frame of the video data;
resizing the first specific image to obtain a second specific image, wherein a size of the second specific image is double of a size of each frame of the video data;
detecting and extracting one or more vector of pose coordinates from the second specific image, wherein the vector of pose coordinates corresponds to a plurality of joints of a body of the user in the second specific image;
computing, via a Chebyshev Distance technique, a distance between (i) the detected one or more vector of pose coordinates and (ii) one or more predefined training vectors of pose coordinates to obtain a plurality of distances, wherein
each distance of the obtained plurality of distances corresponds to each pose coordinate of the one or more pose coordinates, and
the one or more predefined training vectors of pose coordinates are based on:
(i) vector points that identify human poses of a test user which is obtained from a plurality of training activity images, wherein the plurality of training activity images includes at least one of sitting image, a walking image, walking image, and
(ii) a specific activity label of the plurality of training activity images; and
determining a minimum distance among the obtained plurality of distances; and
detecting the second activity based on the determined minimum distance; and validating, via the one or more hardware processors, the first activity and the second activity based on a comparison of
(i) the detected first activity using the activity detection model with an associated timestamp at which the first activity is recorded, and
(ii) the detected second activity based on the based on the determined minimum distance with the associated timestamp at which the second activity is recorded;

obtaining a true positive or a false positive result related to the first activity and the second activity based on comparison of:
the detected first activity using the activity detection model, and
the detected second activity based on the based on the determined minimum distance, wherein false positive result indicates that:
the first activity is different from the second activity, and
one of the first activity or the second activity is not deemed to have occurred at the associated timestamp.

12. The computer program product comprising the non-transitory computer readable medium as claimed in claim 11, further comprising the second specific image based on a specification of each frame of the video data.

13. The computer program product comprising the non-transitory computer readable medium as claimed in claim 11, wherein the one or more pre-defined training vectors of pose coordinates are obtained by:
obtaining, via the one or more hardware processors, training video data that is captured from a specific image capturing device, wherein the training video data comprises specific information specific to one or specific more users, wherein the one or more specific user are different from the user;
tagging, via the one or more hardware processors, an activity label for each activity identified in one or more frames of the training video data;
processing, via the one or more hardware processors, each of the one or more frames of the training video data to extract a training image of the one or more users; and
generating, via the one or more hardware processors, the one or more pre-defined training vectors of pose coordinates using the training image of the one or more specific users.

14. The computer program product comprising the non-transitory computer readable medium as claimed in claim 11, further comprises:
performing, via the one or more hardware processors, a comparison of each computed distance across the plurality of computed distances; and
detecting, via the one or more hardware processors, the second activity based on the comparison.

* * * * *